US009937097B2

(12) United States Patent
Lenke

(10) Patent No.: US 9,937,097 B2

(45) **Date of Patent: *Apr. 10, 2018**

(54) STIMULATION DEVICE HAVING AN APPENDAGE

(71) Applicant: NOVOLUTO GmbH, Metten (DE)

(72) Inventor: Michael Lenke, Metten (DE)

(73) Assignee: NOVOLUTO GMBH, Metten (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/487,123

(22) Filed: Apr. 13, 2017

(65) Prior Publication Data

US 2017/0216135 A1 Aug. 3, 2017

Related U.S. Application Data

(63) Continuation of application No. 15/302,981, filed as application No. PCT/EP2015/067017 on Jul. 24, 2015.

(30) Foreign Application Priority Data

Mar. 13, 2015 (DE) ........................ 10 2015 103 694

(51) Int. Cl.

*A61F 5/00* (2006.01)

*A61H 19/00* (2006.01)

(Continued)

(52) U.S. Cl.

CPC ........... *A61H 19/34* (2013.01); *A61H 9/0057* (2013.01); *A61H 19/44* (2013.01); *A61H 23/02* (2013.01);

(Continued)

(58) Field of Classification Search

CPC ........ A61H 19/00; A61H 19/30; A61H 19/34; A61H 19/40; A61H 19/44; A61H 23/00; A61H 9/0057

(Continued)

(56) References Cited

U.S. PATENT DOCUMENTS 1,730,535 A 10/1929 Rudolph
1,882,040 A 10/1932 Roehm (Continued)

FOREIGN PATENT DOCUMENTS

CN 2153352 Y 1/1994
CN 2198900 Y 5/1995

(Continued)

OTHER PUBLICATIONS

International Search Report and Written Opinion dated Jul. 22, 2016, in connection with International Patent Application No. PCT/EP2015/067017, 29 pages.

(Continued)

*Primary Examiner* — John Lacyk

(74) *Attorney, Agent, or Firm* — Chiesa Shahinian & Giantomasi PC

(57) ABSTRACT

A stimulation device is provided in accordance with one embodiment. The stimulation device includes a chamber which has a flexible wall portion. A drive unit of the stimulation device is in physical communication with the flexible wall portion so as to cause deflections of the flexible wall portion in opposing directions, thereby resulting in a changing volume of the chamber. The changing volume of the chamber results in modulated positive and negative pressures with respect to a reference pressure. An opening of the stimulation device is for applying the modulated positive and negative pressures to a body part. An appendage of the stimulation device may be used as a handle to allow a user to position the stimulation device over the body part. The stimulation device includes a control device for controlling the drive unit.

30 Claims, 7 Drawing Sheets

(51) Int. Cl.
*A61H 9/00* (2006.01)
*A61H 23/02* (2006.01)

(52) U.S. Cl.
CPC ................ *A61H 2201/0107* (2013.01); *A61H 2201/0188* (2013.01); *A61H 2201/0192* (2013.01); *A61H 2201/5097* (2013.01)

(58) Field of Classification Search
USPC ........................................................... 600/38
See application file for complete search history.

(56) References Cited

U.S. PATENT DOCUMENTS

| | | | |
|---|---|---|---|
| 1,898,652 | A | 2/1933 | Williams |
| 1,964,590 | A | 6/1934 | Friederich |
| 2,017,284 | A | 10/1935 | Lembright |
| 2,076,410 | A | 4/1937 | McGerry |
| 2,112,646 | A | 3/1938 | Biederman |
| 2,154,427 | A | 4/1939 | Andres |
| 2,234,102 | A | 3/1941 | Andres |
| 2,314,590 | A | 3/1943 | McCarty |
| 2,519,790 | A | 8/1950 | Quinn |
| 2,561,034 | A | 7/1951 | Phillips |
| 3,396,720 | A | 8/1968 | Shigeyuki |
| 3,906,940 | A | 9/1975 | Kawada |
| 3,910,262 | A | 10/1975 | Stoughton |
| 4,088,128 | A | 5/1978 | Mabuchi |
| 4,203,431 | A | 5/1980 | Abura et al. |
| 4,428,368 | A | 1/1984 | Torii |
| 4,900,316 | A | 2/1990 | Yamamoto |
| 5,003,966 | A | 4/1991 | Saka et al. |
| 5,377,701 | A | 1/1995 | Fang |
| 5,377,702 | A | 1/1995 | Sakurai |
| 5,593,381 | A | 1/1997 | Tannenbaum et al. |
| 6,099,463 | A | 8/2000 | Hockhalter |
| 6,319,211 | B1 | 11/2001 | Ito et al. |
| 6,464,653 | B1 | 10/2002 | Hovland et al. |
| 6,733,438 | B1 | 5/2004 | Dann et al. |
| 7,079,898 | B2 | 7/2006 | Cohn |
| 2001/0041848 | A1 | 11/2001 | Ito et al. |
| 2002/0120219 | A1 | 8/2002 | Hovland et al. |
| 2002/0198488 | A1 | 12/2002 | Yao |
| 2003/0114804 | A1 | 6/2003 | Putzer |
| 2004/0236254 | A1 | 11/2004 | Nichols |
| 2004/0260209 | A1 | 12/2004 | Ella et al. |
| 2005/0159684 | A1 | 7/2005 | Ikadai |
| 2006/0089572 | A1 | 4/2006 | Byon |
| 2006/0116612 | A1 | 6/2006 | Drysdale |
| 2007/0100259 | A1 | 5/2007 | Nan |
| 2008/0071138 | A1 | 3/2008 | Mertens et al. |
| 2008/0106896 | A1 | 5/2008 | Liu et al. |
| 2008/0304984 | A1 | 12/2008 | Chan |
| 2008/0312674 | A1 | 12/2008 | Chen et al. |
| 2009/0048581 | A1 | 2/2009 | Sebban |
| 2009/0118573 | A1 | 5/2009 | Tsao |
| 2010/0298745 | A1 | 11/2010 | Liu et al. |
| 2011/0295162 | A1 | 12/2011 | Chang et al. |
| 2013/0012769 | A1 | 1/2013 | Carlson |
| 2013/0116503 | A1 | 5/2013 | Mertens et al. |
| 2014/0142374 | A1 | 5/2014 | Makower et al. |
| 2014/0309565 | A1 | 10/2014 | Allen |
| 2016/0213557 | A1 | 7/2016 | Lenke |
| 2017/0065483 | A1 | 3/2017 | Lenke |

FOREIGN PATENT DOCUMENTS

| | | | |
|---|---|---|---|
| CN | 101848688 | A | 9/2010 |
| CN | 102151219 | A | 8/2011 |
| CN | 202154785 | U | 3/2012 |
| CN | 102600034 | A | 7/2012 |
| CN | 102743275 | A | 10/2012 |
| CN | 102743276 | A | 10/2012 |
| CN | 103517697 | A | 1/2014 |
| CN | 103961246 | A | 8/2014 |
| CN | 104248500 | A | 12/2014 |
| CN | 204931954 | U | 1/2016 |
| CN | 205494128 | U | 8/2016 |
| DE | 582196 | | 8/1933 |
| DE | 1463673 | U | 2/1939 |
| DE | 1703184 | U | 7/1955 |
| DE | 3222467 | A1 | 12/1983 |
| DE | 9309994.0 | | 11/1993 |
| DE | 4243876 | A1 | 6/1994 |
| DE | 10011289 | A1 | 9/2001 |
| DE | 20112384 | U1 | 10/2001 |
| DE | 19853353 | C2 | 5/2002 |
| DE | 102004017702 | A1 | 10/2005 |
| DE | 202012005414 | U1 | 8/2012 |
| DE | 212013000027 | U1 | 9/2014 |
| EP | 0365230 | A2 | 4/1990 |
| EP | 1554947 | B1 | 7/2005 |
| EP | 2042147 | A1 | 4/2009 |
| EP | 2712601 | A1 | 4/2014 |
| JP | 53135768 | | 11/1978 |
| JP | 53149442 | | 12/1978 |
| JP | 54115952 | B2 | 9/1979 |
| JP | 57099986 | A | 6/1982 |
| JP | H05037234 | U | 5/1993 |
| JP | 2000197518 | A | 7/2000 |
| JP | 2008-125577 | | 6/2008 |
| WO | 3205758 | A1 | 4/1992 |
| WO | 2000/28939 | A2 | 5/2000 |
| WO | 2004004610 | A1 | 1/2004 |
| WO | 2006058291 | A2 | 6/2006 |
| WO | 2008028076 | A2 | 3/2008 |
| WO | 2013178223 | A2 | 12/2013 |
| WO | 2014131110 | A1 | 9/2014 |
| WO | 2015039787 | A1 | 3/2015 |

OTHER PUBLICATIONS

International Search Report and Written Opinion dated Sep. 25, 2014, in connection with International Patent Application No. PCT/EP2014/065734, 14 pages.

"Sex hilft gegen Erkältung," Focus Online, Dec. 5, 2004, 2 pages.

"Gesundheitsminister: Mehr Sex gegen Bluthochdruck," http://www.heilpraxisnet.delnaturheilpraxis/sex-gegen-bluthochdruck-665.php, Apr. 27, 2010.

Beate Lakotta, Schmerz und Glückseligkeit, Der Spiegel, pp. 136-138, Jun. 2006.

Maria M. Kettenring, "Erotische Partnermassage", Gräfe und Unser Publishers, 2004, 4 pp.

Nonfinal Office Action dated Aug. 26, 2016 by the United States Patent and Trademark Office in connection with U.S. Appl. No. 15/023,471, 25 pp.

Final Office Action dated Jan. 6, 2017 by the United States Patent and Trademark Office in connection with U.S. Appl. No. 15/023,471, 28 pp.

Nonfinal Office Action dated Feb. 24, 2017 by the United States Patent and Trademark Office in connection with U.S. Appl. No. 15/354,599, 38 pp.

Examination Report dated Dec. 20, 2017 from Australian Patent Application No. 2017228536; 5 pages.

Document submitted in opposition of German Patent No. 102013110501.7 on Jan. 24, 2018; 34 pages.

STIMULATION DEVICE HAVING AN APPENDAGE

CROSS-REFERENCE TO RELATED APPLICATIONS

This application is a continuation of U.S. patent application Ser. No. 15/302,981, filed Oct. 7, 2016, which is a national stage (under 35 U.S.C. 371) of International Patent Application No. PCT/EP2015/67017, filed Jul. 24, 2015, which claims priority to German Patent Application No. 102015103694.0, filed Mar. 13, 2015, the disclosures of which are herein incorporated by reference in their entirety.

TECHNICAL FIELD

The present invention relates to a stimulation device having an appendage for erogenous zones, in particular for the clitoris, a system with a stimulation device, and methods for stimulating body parts.

BACKGROUND

The erogenous zones of the human body can be stimulated with a variety of aids. For example, vibrators are used to apply a stimulus to a particular area of the skin by direct contact. These include stimulation aids for insertion into the human body, such as dildos.

Direct stimulation of the clitoris, for example using a clitoral massage vibrator, is frequently problematic. The clitoris is usually a woman's most sensitive erogenous zone. The entire clitoris is highly innervated, making it particularly touch-sensitive and responsive to sexual stimuli. In this context, the clitoral glans, in which the nerve cords of the two crura meet, should be emphasized in particular. Thus, on the one hand frequent application of a clitoral massage vibrator for direct stimulation leads to habituation effects or conditioning of the stimulated erogenous zone, while on the other the first applications of such a device may require certain practice or familiarization. Moreover, indirect stimulation of the female erogenous zones may be insufficient, or it may be desired to intensity the stimulation effect.

Furthermore, medical studies conducted in 2006 identified the female clitoris as the definitive starting point of the female climax, and for the first time neurologically proved the different qualities of sensation of clitoral and vaginal orgasm. Thus, both the clitoris and the vagina are capable of orgasm.

Furthermore, the sensitivity of the human erogenous zones, such as the clitoris, the inner and outer labia or the nipples, differs greatly from one individual to the next. Moreover, the sensitivity of the corresponding zone can change dramatically from one situation to another or even during a sexual act. Furthermore, a rapid and pronounced stimulation of different erogenous zones is frequently desired.

Various direct and indirect forms of stimulation are usual practice, for example vacuum pumps and dildos.

For indirect stimulation of erogenous zones, and particularly the clitoris, conventional vacuum devices are used to stimulate the erogenous zones of the person concerned without directly contacting the main area to be stimulated. Thus, for example, vacuum pumps for the primary or secondary female sexual organs are known, which usually have a suction cup for placing on the appropriate area and a hand pump. The negative pressure exerted by this type of device on the clitoris, for example, generates a negative pressure in the clitoris itself which is usually below the systolic blood pressure. This difference in pressure results in an enlargement of the clitoris and/or stimulates the blood flow in the affected area. This vascular clitoral engorgement serves both to promote desire by increasing sensitivity and for visual and tactile manipulation. The improved blood circulation also results in an increased secretion of vaginal moisture, which makes the stimulation more pleasurable. However, the manual operation of the hand pump is often onerous or irksome. In addition, the long-term or uninterrupted application of negative pressure with this device category too may result in habituation effects, which limit the effectiveness of the device in the long term.

Electrically driven vacuum pumps are also increasingly used instead of a manually operated vacuum pump. As an example of this, WO 2006/05 82 91 A2 discloses a device for sexual therapy, wherein the arrangement comprises a tubular suction chamber for the clitoris, an electrical vacuum source (vacuum pump) and a plurality of air flow openings. Operation of the vacuum pump generates an ongoing air flow or air exchange in the chamber, in the area of the clitoris. This has the disadvantageous effect of drawing off by suction the vaginal moisture, which is increased as a result of the negative pressure, thus having a drying effect on the stimulated skin parts. Likewise, the drawn-off moist air results in contamination of the fluidically downstream vacuum arrangement, for example the vacuum pump. Such arrangements with vacuum pumps may thus be problematic from the point of view of hygiene, as vacuum pumps and the associated valves or ventilation components often have dead spaces and/or are difficult to clean. Furthermore, the device serves to treat the blood vessels in the clitoris and not to provide stimulation up to sexual climax.

U.S. Pat. No. 6,464,653 B1 discloses therapeutic devices and methods that generate a clitoral engorgement with the aid of a vacuum generated by a vacuum pump to assist in the treatment of clitoral disorders such as incontinence. A control valve or modulator that can be appropriately covered by a finger is used to manually adjust or vary the level of vacuum in the suction chamber. This requires the user's attention and may be irksome or distracting under certain circumstances. This relatively complex device having further valves also has the disadvantages relating to hygiene and dehydration that were mentioned above, with the device moreover serving for long-term therapeutic purposes and not for short-term sexual stimulation.

Thus, the devices of the prior art have the common disadvantage that the complexity of the arrangements generating negative pressure or positive pressure may be high and this device may have problems in respect of hygiene. Moreover, there is a problem of ease of handling the devices, which are frequently uncomfortable to hold and/or require habituation.

Furthermore, the devices of the prior art have the further common disadvantage in that habituation effects occur in the event of long-term, continuous or frequently recurring application of negative pressures.

Another disadvantage of some of the previously described vacuum devices is, firstly, that the negative pressure has to be limited by means of a control valve or a vacuum pump and, secondly, that the negative pressure is supposed to be relieved by means of manually opening a release valve before the suction cup is detached from the skin. Should one of the valves have a technical defect and/or the user operate the device incorrectly, there is a risk of injury in certain circumstances.

Thus, in view of the problems mentioned above, one object of the embodiments described herein is to provide a stimulation device that has a simple construction, is easy and safe to use, and has a pronounced stimulation effect.

This object is achieved by the stimulation device as described herein. Advantageous developments and embodiments are also described herein.

SUMMARY

A stimulation device is provided in accordance with one embodiment. The stimulation device includes a chamber which has a flexible wall portion. In one embodiment, the flexible wall portion may include silicon and may be integral with the chamber. A drive unit of the stimulation device is in physical communication with the flexible wall portion so as to cause deflections of the flexible wall portion in opposing directions, thereby resulting in a changing volume of the chamber. The changing volume of the chamber results in modulated positive and negative pressures with respect to a reference pressure. The modulated positive and negative pressures are applied to a body part (e.g., a clitoris) through an opening of the stimulation device. For example, the opening of the stimulation device may be placed over the body part to apply the modulated positive and negative pressures. The stimulation device may include an appendage, which can be used as a handle to allow a user to hold and position the stimulation device over the body part. The drive unit is controlled by a control device of the stimulation device.

In one embodiment, the stimulation device includes a second chamber. The changing volume of the chamber results in the modulated positive and negative pressures in the second chamber.

In one embodiment, the stimulation device is rigid such that the stimulation device does not significantly bend. The stimulation device may be a portable, hand-held, battery powered device. The stimulation device may also have an operating element for adjusting the modulated positive and negative pressures and a light emitting diode for indicating a status of the stimulation device.

In accordance with an embodiment, the stimulation device includes a pressure field generator which has a flexible wall portion. A drive unit of the stimulation device is in physical communication with the flexible wall portion so as to cause deflections of the flexible wall portion in opposing directions, thereby resulting in a changing volume of the pressure field generator. The changing volume of the pressure field generator results in modulated positive and negative pressures with respect to a reference pressure. The modulated positive and negative pressures are applied to a body part through an opening of the stimulation device. The stimulation device may include an appendage, which can be used as a handle to allow a user to hold and position the stimulation device over the body part. The drive unit is controlled by a control device of the stimulation device.

In one embodiment, the pressure field generator includes a first chamber and a second chamber. As such, deflections in the flexible wall portion of the first chamber of the pressure field generator result in the modulated positive and negative pressures in the second chamber of the pressure field generator.

The above-described features and functions of the present invention, and further aspects and features, are further described below with the aid of a detailed description of preferred embodiments with reference to the attached illustrations.

DESCRIPTION OF PREFERRED EMBODIMENTS

Figure 1:
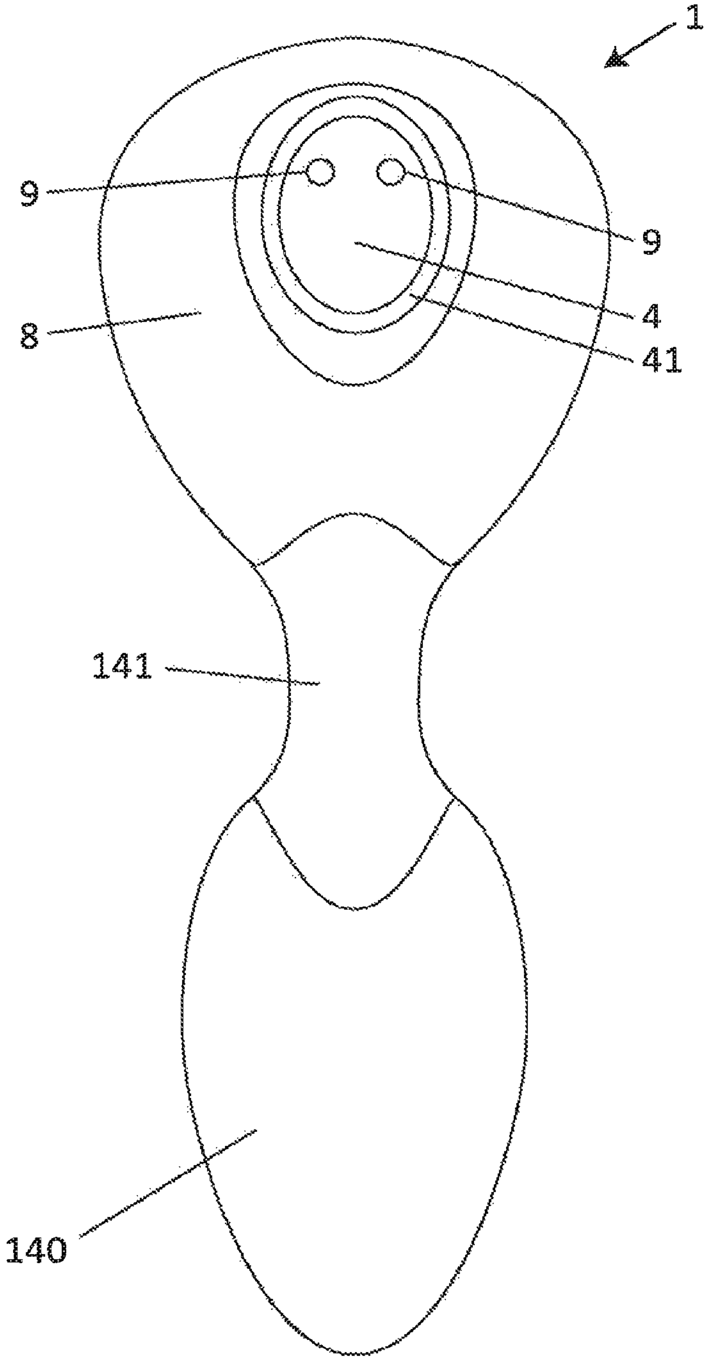
FIG. 1 shows a front view of a first embodiment of the stimulation device according to the invention, with an appendage in a straight position.

According to one embodiment, a pressure field generating arrangement of the stimulation device has at least one first chamber and at least one second chamber having at least one opening for placing on a body part or on the erogenous zone and at least one connection element that connects the first chamber to the second chamber.

In one embodiment the chambers are in fluidic communication via the at least one connection element to allow the simple generation of a pressure field in the second chamber by changing the volume in the first chamber and temporarily direct the generated pressure field to the area of skin to be stimulated.

A pressure field, in the context of the embodiments described herein, is a field of medium pressures that is variable over time and has temporary positive pressures and temporary negative pressures, a negative pressure being a pressure of medium that is below the reference pressure and a positive pressure being a pressure of medium that is above the reference pressure. As a result, the medium flows back and forth in the pressure field. Thus, preferably a (largely) intermittent exchange of said medium can occur.

The medium is usually gaseous, preferably air, but may for example alternatively or in addition be a liquid medium, such as water or commercially available lubricant. For example, the chambers may be filled with the lubricant prior to using the stimulation device. This also allows the corresponding area of skin to be stimulated with a suitable skin-friendly liquid instead of air, which may be desired, depending on the user's individual preference. As a further example, the stimulation device may also be used under water with water as the medium (in the bathtub, for example). In this case the stimulation device is waterproof in form.

The reference pressure is usually the atmospheric pressure acting on the stimulation device that prevails when application begins (i.e. prior to placing the stimulation device on the area of skin to be stimulated). In the preferred application of the stimulation device with air, the reference pressure is the currently prevailing air pressure or normal pressure. For example, when the device is applied under the normal standard conditions the reference pressure may be approximately 1 bar, from which it follows that a negative pressure may be for example 0.7 bar and a positive pressure may be for example 1.3 bar.

The pressure field according to one embodiment is used on the one hand to excite blood circulation of the area of skin to be stimulated, while on the other said area of skin is indirectly massaged. This combines two advantageous effects. The increased blood circulation makes the erogenous zone of the person concerned more sensitive, while moreover generating a massaging effect that serves to stimulate the erogenous zone, for example for sexual arousal up to climax. The massaging effect is generated by the kinetic energy of the medium flowing out of the first chamber through the connection element against the surface of the area of skin to be stimulated. In this way, the massaging effect created by the pressure field is generated indirectly, i.e. without the skin part to be stimulated being in direct contact with a solid body such as a vibrator.

By the exemplary application to the clitoris of the pressure field which is variable over time according to one embodiment, the pressure field imitates a stimulation that usually occurs during sexual intercourse. Likewise, the motion of congress during this generates a varying stimulus of the clitoris. It is thus a lifelike simulation of the natural act of congress, with medical findings confirming that application of the pressure field causes neither habituation effects nor addiction. This is due in particular to the alternating application of negative and positive pressures (or indeed to the non-continuous application of only one type of pressure).

Furthermore, the maximum applicable pressure is typically limited by the maximum load that may be put on the area of skin to be stimulated. Thus, for instance, too high a negative pressure harbors the risk of painful injury, in particular in erogenous zones. Stimulation devices working only with negative pressures are usually limited to this maximum in their mode of operation. By contrast, according to the embodiments described herein, the combination of positive and negative pressures creates an extended operational range of the stimulation-triggering pressure field or effect, as the operational range of the pressure can now be exploited to the maximum in both the positive and the negative range.

The orientation of the at least one connection element towards the area of skin to be stimulated allows the pressure field to work directly, the pressure field being decisively affected by the configuration of the at least one connection element and the at least one opening from the connection element into the second chamber, and is thus adjustable depending on the application of the stimulation device. Thus, the at least one opening of the connection element may be located opposite, preferably directly opposite, the body part to be stimulated. For example, the connection element in a stimulation device intended for the clitoris may have, between the first and second chamber, a single passage opening having a nozzle effect on the clitoral glans. Alternatively, the at least one connection element may comprise a plurality of passage openings, for example four, between the chambers if a relatively large area of skin is to be stimulated.

Furthermore, after placing the halfway or partially opened second chamber on the area of skin to be stimulated, a closed system of medium or air flow is created in the pressure field generating arrangement. Thus, the medium or air is moved decisively back and forth between the chambers, while an exchange with medium or air from outside the system is at least largely avoided. Thus, the first chamber is preferably connected exclusively to the second chamber via or through the connection element. Thus, the first chamber has no connections other than those to the second chamber; for example, there is no direct connection between the first chamber and the environment surrounding the device via a pressure valve or an air discharge channel.

For example, the temperature of the air in the flow system according to one embodiment rapidly adjusts to skin temperature, while the irksome supply of new (possibly cold) air from outside the system, as may be the case when using vacuum pumps of the prior art inter alia, is avoided. Drying effects are moreover avoided, as very little or no removal of stimulation-promoting fluid, such as bodily fluid, occurs in a closed system.

Furthermore, due to the simple construction, the pressure field generating arrangement according to one embodiment has the advantage of better hygiene and improved cleaning capacity. Here, the pressure field generating arrangement avoids valves or pumps/compressors with potential dead spaces and places that cannot be cleaned. The pressure field generating arrangement is thus easy to clean. For example, the stimulation device can be cleaned in a simple manner by filling the first chamber with a cleaning agent and activating the pressure field. Alternatively, the second chamber can be arranged to be replaceable, which also simplifies the cleaning of both chambers. Furthermore, the chambers and the connection element of the pressure field generating arrangement can be manufactured in one piece, wherein they are made for example of a single plastic molded part (e.g. rubber). As a further alternative, the first chamber, the second chamber and the connection element may be made in one piece.

Moreover, the construction according to one embodiment has the result of avoiding complex fluid engineering elements such as valves, which results in simplified manufacture.

Furthermore, the stimulation device according to one embodiment has a drive unit that varies the volume of the first chamber such that a pressure field is generated via the connection element in the second chamber, this pressure field serving to stimulate the erogenous zone, and a control device that activates the drive unit.

The principle of the embodiments described herein means that the medium transported between the chambers is limited in volume to the maximum volume of the first chamber. Moreover, the transported volume can be further limited, as a result of its construction, by the maximum possible change in volume brought about by the drive unit.

Consequently, the maximum positive or negative pressure the stimulation device can build up in the second chamber is limited due to the dimensions of the components of the pressure field generating arrangement and the drive. In particular, the maximum positive or negative pressure can be limited to an amount that minimizes or rules out any risk of injury for the areas of skin to be stimulated. As a result, a safety valve that is usual in the prior art, or a manual intervention in the stimulation process by the user, such as the opening of a release valve, is for example rendered unnecessary.

Furthermore, the variation over time in the pressure field or the modulation of the pressure field by the control device is controlled largely automatically. Thus, the modulation of the pressure field, such as intensity, time profile or sequence, can be previously stored in the control device. Preferably, the variation over time in the pressure field can have a regular or recurring (stimulation) pattern, such as pulses at a predetermined cycle rate or regularly alternating pulse sequences. This allows the user's interaction with the stimulation device to be limited to switching on and off and selecting the stimulation pattern, while the stimulation device automatically executes the preferred stimulation pattern. Thus, the complexity of using the stimulation device is low, particularly when compared with conventional (medical) vacuum stimulation devices. Alternatively or in addition, the stimulation pattern of the stimulation device can be individually configured by the user during or before operation.

Moreover, according to one embodiment, the stimulation device is provided with (at least) one appendage. On the one hand this appendage may be used as a handle in order to hold the stimulation device easily and comfortably, and on the other the appendage may also be used as a direct stimulation aid for insertion into the human body or indeed for placing on the human body.

If the appendage is inserted into the human body, it serves for direct stimulation of the body part concerned. Thus, it supplements the indirect stimulation effect of the pressure field generating arrangement. It is thus possible for a direct and an indirect stimulation of a plurality of erogenous zones to occur simultaneously or alternately. For example, the appendage may be inserted into the female vagina, while stimulation of the clitoris may take place at the same time or alternately by means of the pressure field according to one embodiment. Accordingly, the principle of the combined direct and indirect stimulation may also be applied to other body parts, or the erogenous zones thereof. For example, the appendage may be placed on a woman's clitoris while the pressure field generating arrangement stimulates another woman's or the same woman's clitoris.

In this way, the stimulation device having an appendage may be used by only one person or indeed by two different people for the stimulation of a plurality of erogenous zones.

The combination of direct and indirect stimulation results in an improvement in the stimulation effect and a versatile applicability of the stimulation device. Moreover, further, alternative types of play during the sexual act are possible using the inventive stimulation device having an appendage.

Thus, according to one embodiment, a stimulation device which has a plurality of cumulative orgasm- or stimulation-triggering effects and is suitable for the stimulation of a plurality of erogenous zones, in particular the female clitoris, is provided. Furthermore, a device is provided which avoids dehydration of the erogenous zones to be stimulated, is hygienic and avoids habituation effects.

According to one embodiment, the appendage is movable with the pressure field generating arrangement, for example being connected by means of a joint at one end of the appendage. In this way, the stimulation device may be adapted to the anatomy of the human body in question and to its use. For example, the appendage may be inserted into the female vagina in order then to adapt the angle between the pressure field generating arrangement and the appendage such that the opening of the second chamber can be placed precisely over the clitoris. Consequently, the area of the body between the clitoris and the vagina is stimulated from both sides, mutually enhancing the effects of direct and indirect stimulation.

If the appendage is used as a handle for holding the stimulation device, the angle between the handle and the opening of the second chamber can be adapted to suit the preferences of the user of the device.

According to one embodiment, the appendage is a stimulation aid which is shaped such that the appendage can be inserted into the human body, for example the vagina, for direct stimulation. In this case, the appendage preferably takes the form of a dildo. Here, sharp corners in particular are avoided. Thus, the appendage is preferably in a form such that it can be inserted smoothly into body cavities and/or also remain inserted therein.

According to one embodiment, the appendage is an elongate, lens-shaped or pillow-shaped body which is adapted such that the appendage can be inserted smoothly into the female vagina. This improves the direct stimulation effect.

According to one embodiment, the appendage is mounted on the pressure field generating arrangement such that the stimulation device is unitary in form. Here, unitary means in particular that the stimulation device having an appendage and a pressure field generating arrangement takes the form of an integrated, cohesive device. Preferably, in this case the appendage and the pressure field generating arrangement transition into one another seamlessly. This improves hygiene and operability of the stimulation device.

According to one embodiment, the appendage has a vibration device. This vibration device may be actuated such that the appendage vibrates, as known in the case of electromechanically operated dildos. In this case, the vibration may either be activated independently of the other parts of the stimulation device, or indeed the vibration may be controlled by means of the control device, which in that case controls the drive unit of the pressure field generating arrangement as well. Preferably, the vibration may be controllable in a conventional manner as regards intensity, duration and sequence. The vibration intensifies the direct stimulation effect.

According to one embodiment, a system comprises the stimulation device and a remote control device arranged separately from the stimulation device, wherein the control device of the stimulation device is remotely controlled by the remote control device. This allows a conventional wireless (for example via radio) or wired remote control to be employed in order to allow remote-controlled modulation of the stimulation device or activation thereof by another user.

According to one embodiment, methods for stimulating body parts, in particular the clitoris, are described herein.

The associated advantageous effects are explained in more detail above in relation to the pressure field and the appendage.

According to one embodiment, the stimulation device may be used as a sex toy for stimulating the female clitoris. As explained in the introduction, the female clitoris is a particularly sensitive erogenous zone in women, which is why the use of an indirect massaging stimulation, combined with a negative-pressure stimulation, for this body part for stimulation up to orgasm appears particularly advantageous.

In one embodiment, the methods for stimulating erogenous zones serve for sexual pleasure, and thus the methods do not serve for medical, for example therapeutic, purposes.

Figure 2:
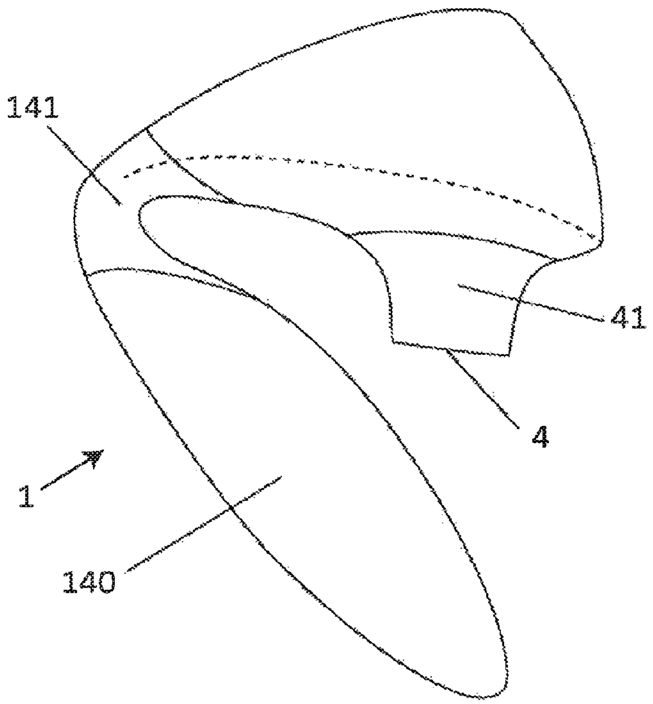
FIG. 2 shows a side view of the first embodiment of the stimulation device according to the invention, with the appendage in an angled position.
Figure 3:
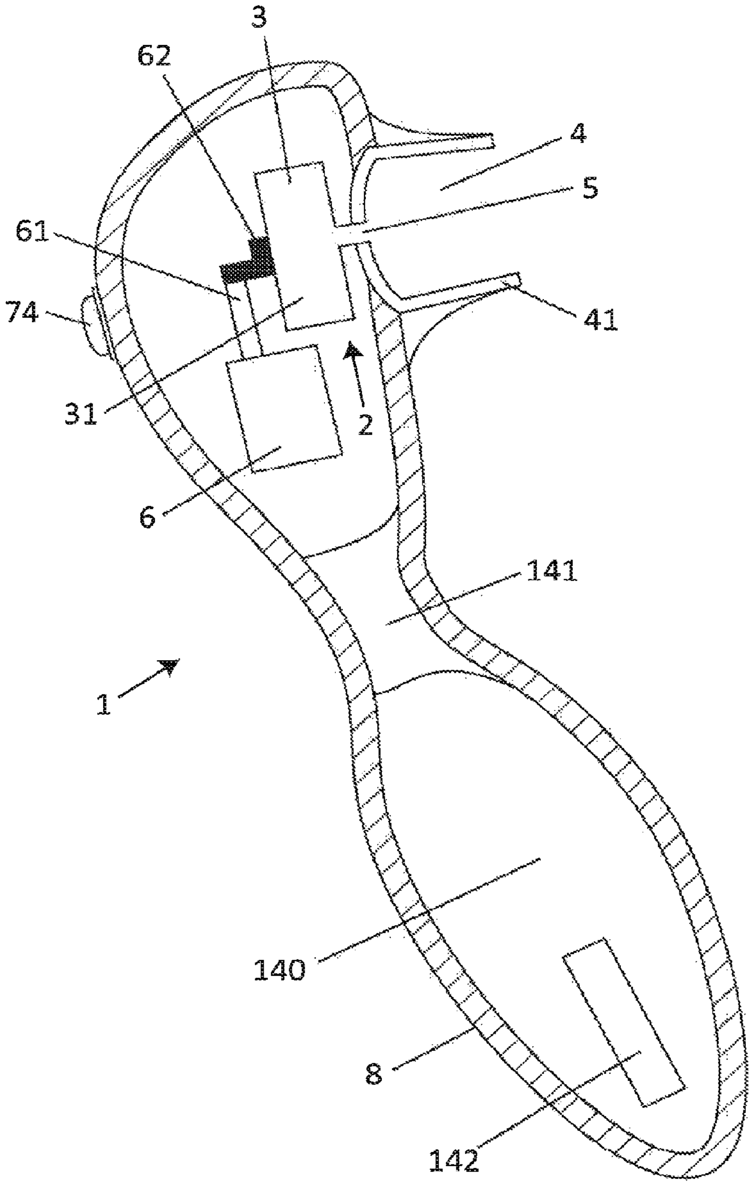
FIG. 3 shows a schematic cross section through the first embodiment of the stimulation device according to the invention.

With reference to FIGS. 1, 2 and 3, a first embodiment will be explained below. FIG. 1 shows a front view of the first embodiment of the stimulation device 1 with an appendage 140 in a straight position, while FIG. 2 further shows a side view of the stimulation device 1 with the appendage 140 in an angled position, and FIG. 3 shows a cross section of the first embodiment of the stimulation device 1.

The first embodiment of the stimulation device 1 is a preferably portable electrical or small device that has a housing 8, a pressure field generating arrangement 2, an optional on/off switch 74 and an optional light 9.

The housing 8 preferably takes an ergonomic form such that it can be held comfortably in one hand and has no sharp or pointed edges. Furthermore, the housing 8 may be made of a plastics material such as polycarbonate (PC) or acrylonitrile butadiene styrene (ABS). Moreover, the gripping areas or even the entire housing may be supplemented by or be made of a silicone which has advantageous tactile properties. The housing 8 preferably takes an at least water-resistant or splash-proof form, for example protection class IP 24. Furthermore, the broken line in FIG. 2 indicates an optional side edge of the housing 8.

The optional on/off switch 74 serves to activate and deactivate the stimulation device 1. This on/off switch 74 may for example be a push button, which switches the stimulation device 1 on or off when held down, or a latching slide switch. Alternatively, it may be possible to switch the stimulation device 1 on and off by remote control.

The pressure field generating arrangement 2 of a first embodiment has a first chamber 3 in the interior of stimulation device 1, a second chamber 4 for placing on a body part 11 to be stimulated, and a connection element 5 that connects the first chamber 3 to the second chamber 4.

A drive unit 6, for example an electric motor, drives the first chamber 3 via a shaft 61 and by means of a cam 62 (or alternatively by means of a connecting rod) such that the volume of the first chamber 3 changes in accordance with rotation of the shaft 61 of the drive unit 6. On this point, it should be noted that any types of drive that cause a deflection of the wall 31 of the first chamber 3 for a change in volume can in principle be used in the stimulation device 1. This may for example be performed hydraulically, pneumatically, piezoelectrically, mechanically or electromagnetically. Examples of this are described in more detail below.

A control device 7 activates the drive unit 6, optional operating elements 71 and at least one optional display 72. Here, the control device 7 and the drive unit 6 are supplied with power for example by the internal battery 76 and/or the external power supply 73.

The stimulation device 1 further has at least one appendage 140. This appendage 140, which is preferably part of the housing 8, may optionally be moved or angled in relation to the housing part in which the pressure field generating arrangement 2 is accommodated. Here, the appendage may be angled or indeed rotated by means of a joint 141. The joint 141 may for example take the form of a plastically deformable plastic part, an adjustable joint or a hinge. FIG. 2 shows an example of a position of the appendage 140 which is angled in relation to the section of the housing 8 of the stimulation device 1 in which the pressure field generating arrangement 2 is accommodated. Alternatively, the appendage may also take a rigid or immovable form.

The appendage 140 is preferably a stimulation aid for insertion into the human body, for example the vagina or other bodily orifices. Here, the appendage 140 is shaped for example as a conventional dildo. Alternatively, the appendage may be constructed such that it is adapted to the human anatomy of another bodily orifice, for example the mouth. Moreover, the appendage 140 may take a form such that it can also be used as a handle in order to hold the stimulation device 1 comfortably.

Moreover, the appendage 140 may optionally have a vibration device 142 that can be capable of being switched on and/or controlled. The vibration device 142 causes the appendage to undergo mechanical vibrations that support the direct stimulation effect of the appendage 140.

Optionally, the appendage 140 is mounted on the section of the housing 8 that accommodates the pressure field generating arrangement 2 such that the (entire) housing 8 of the stimulation device 1 takes a unitary form. In this way, the housing 8 creates the impression of being in one piece, for example by means of flexible and/or seamless connection elements of the housing 8. Alternatively, the housing 8, including the appendage 140, may have a silicone coating.

In a straight or non-angled orientation of the appendage 140, as shown in FIG. 1, the stimulation device 1 can be comfortably held, or indeed inserted into bodily orifices in a simple manner. If the appendage 140 is angled, as shown in FIG. 2, for example after insertion, the opening 42 can thus be guided out of the body part 11 to be stimulated. In this angled position of the stimulation device 1, both a direct and an indirect stimulation of at least one erogenous zone of the body can take place simultaneously. In this case, the body part 11 to be stimulated is located between the appendage 140 and the pressure field generating arrangement 2.

Furthermore, an optional light 9 can be provided on or in the housing 8. Here, the light 9 preferably serves for lighting the interior of the second chamber 4. The light 9 can either be switched on by the user or automatically activated when the stimulation device 1 is activated. Furthermore, the light 9 can take the form of energy-saving light emitting diodes. The light can for example serve in the dark as an orientation aid for the user of the stimulation device 1, or as additional visual stimulation.

Figure 4:
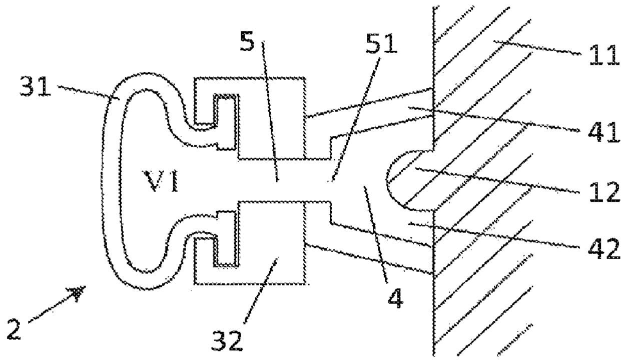
FIG. 4 shows a cross section through a pressure field generating arrangement of a first aspect of the present invention, in the first state.
Figure 5:
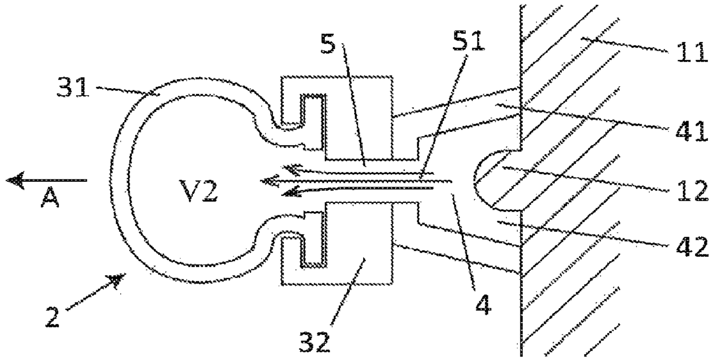
FIG. 5 shows a cross section through a pressure field generating arrangement of a first aspect of the present invention, in the second state.
Figure 6:
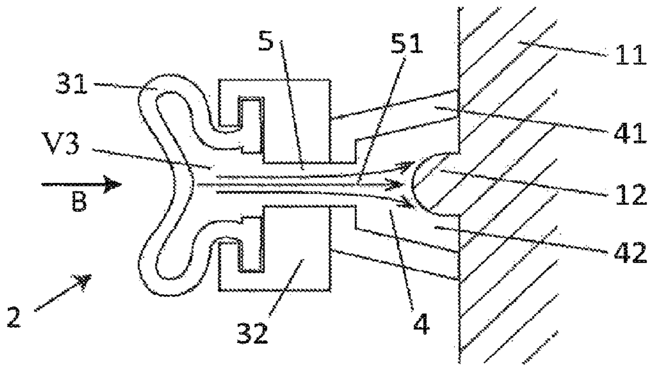
FIG. 6 shows a cross section through a pressure field generating arrangement of a first aspect of the present invention, in the third state.

With reference to FIGS. 4, 5 and 6, the construction and function of a first aspect of the pressure field generating arrangement 2 of the stimulation device 1 will be described below in more detail.

FIG. 4 shows the pressure field generating arrangement 2 in a first state, with the second chamber 4 placed on the area of skin or body part 11 to be stimulated. The first state of the pressure field generating arrangement 2 is characterized by a neutral deflection of the first chamber 3, i.e. no external force acts on the first chamber 3, for example from the drive unit. Here, the volume V1 of the first chamber is the standard volume of this chamber 3.

The body part 11 to be stimulated is an area of skin on the body, wherein here for example a particularly sensitive erogenous zone, the clitoris 12, is shown. Thus, use of the stimulation device 1 is not limited to the female clitoris 12, however; rather, the stimulation device 1 can be applied to all body parts or erogenous zones (such as the inside of the thighs, lumbar region, nape of the neck, nipples, etc.) which can be stimulated by means of medium- or air-pressure massage and/or negative pressure.

Because it is placed on the body part 11 to be stimulated, the second chamber 4 forms a chamber that is largely or completely closed off from the exterior of the pressure field generating arrangement 2 and whereof the only remaining connection to the second chamber is via the connection element 5, wherein the edges of chamber 4 ideally form an air-tight enclosure with the surface of the body part 11. Two communicating chambers 3 and 4 are created in this way, wherein a corresponding pressure equalization between the chambers 3 and 4 via the connection element 5 occurs in the event of a change in volume in one of the chambers 3 or 4.

A wall 31 of the first chamber 3 is secured by means of a holder 32. The holder 32 is in turn attached to the housing 8. The wall 41 of the second chamber is furthermore mounted on the holder 32. Two mutually aligned openings in the wall 41 of the second chamber and the holder 32 together form the connection element 5, which connects the first chamber 3 and the second chamber 4. In this arrangement, the wall 31, the holder 32 and the wall 41 are preferably joined to each other by adhesion to be medium- or air-tight. Alternatively, they can also be press-fitted or screwed to each other (for example with the aid of sealing areas between the housing 8 and the respective part). The holder 32 can also be joined to the housing 8 for example by adhesion or screws.

The wall 31 of the first chamber 3 is preferably made of a flexible medium- or air-tight material such as rubber. The holder 32 is preferably made of a rigid plastics material which is likewise medium- or air-tight. The wall 41 of the second chamber is preferably made of a flexible, skin-friendly material such as silicone or rubber.

FIG. 5 shows the pressure field generating arrangement 2 of FIG. 4 in a second state, wherein the second chamber 4 is once again placed on the body part 11 to be stimulated. The second state is characterized in that a force A acting on the first chamber 3 causes the chamber 3 to expand. To be precise, in this exemplary embodiment the force A draws the wall 31 of the first chamber 3 in a direction away from the second chamber 4.

This increases the volume V2 in the chamber 3, i.e. V2>V1. To equalize the difference in pressure created between the chambers 3 and 4, the medium or air now flows from the second chamber 4 into the first chamber 3.

Assuming that in the first state the pressure in the chambers 3 and 4 corresponds to the currently prevailing external reference pressure (air pressure for example), the overall pressure that is present in the second state will be lower than the external reference pressure. This negative pressure is set such that it is preferably lower than the usual systolic blood pressure in the blood vessels of the body part 11. The blood circulation in this area thus increases, and the clitoris 12 is better supplied with blood in the second state.

FIG. 6 shows the pressure field generating arrangement 2 in a third state, wherein the second chamber 4 is once again placed on the body part 11 to be stimulated. The third state is characterized in that a force B acting on the first chamber 3 causes a volume reduction or compression in the chamber 3. To be precise, the direction of the force B is opposed to the direction of the force A and deforms the wall 31 of the first chamber such that the resulting volume V3 of the chamber is smaller than the volume V1. The compression of the chamber 3 causes a positive pressure in the chamber 3, which is equalized by a medium or air flow through the connection element 5 in the direction of the second chamber 4.

This flow of medium is now preferably directed, by the orientation of the opening 51 and/or of the connection element 5, towards the body part 11 to be stimulated, in particular towards the glans of the clitoris 12. The indirect (pressure) massage according to one embodiment occurs as a result of the medium flowing onto the body part 11. The size of the opening 51 is in this case dimensioned such that it is small enough in relation to the volume displaced in the first chamber 3 to sufficiently accelerate the medium for a perceptible massaging effect.

Furthermore, the type of flow can not only be advantageously influenced by the size and orientation of the opening 51 but also by the inner configuration of the connection element. For example, helical grooves in the connection element 5 can cause the flow according to one embodiment to swirl, wherein the flow profile develops a "softer" or more turbulent action on the body part to be stimulated. Alternatively, the pressure field produced in the second chamber 4 can be adjusted to suit the application by means of a plurality of openings 51.

The advantage of the arrangement shown in FIGS. 4 to 6 is that it is unproblematic from the point of view of hygiene (because dead spaces are avoided, for example) and is simple to manufacture. For example, no valves or further openings in or on the first chamber 3 are required.

Figure 7:
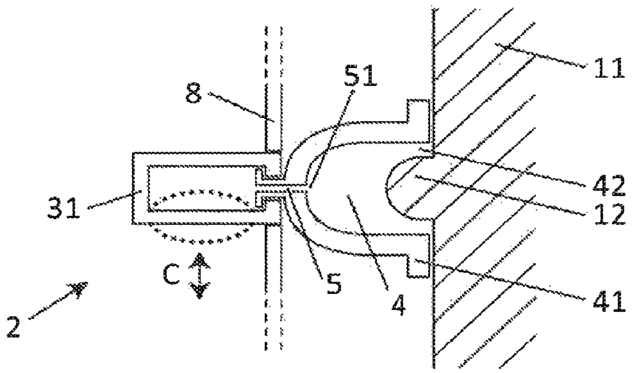
FIG. 7 shows a cross section through a pressure field generating arrangement of a second aspect of the present invention.

FIG. 7 shows a second aspect with an alternative construction of the pressure field generating arrangement 2. Here, the walls 31 and 41 of the first and second chambers 3 and 4 can engage with one another such that, as in the first aspect of construction of the pressure field generating arrangement 2, they form two communicating chambers with a connection element 5. Thus, a separate holder is not required, while the second chamber 4 is replaceable. Moreover, the connection element 5 can take a form integral or in one piece with the wall 41 of the second chamber 4. A replaceable chamber 4 has the advantage that in this way various shapes of the chamber 4 that are adjusted to the respective body part can be used (a more detailed description thereof is provided below) without the need to replace the entire stimulation device 1. Alternatively, the second chamber 4 can also be attached to the housing 8 by being pushed on (not shown in more detail). The wall 31 of the first chamber 3 can be joined to the housing 8 by adhesion or screws for example.

It is also possible, as shown in more detail in FIG. 7 by the broken line and the double arrow C, for the first chamber 3 to be expanded and compressed by a force acting perpendicularly to the axial direction of the connection element 5. In principle, the force exerted indirectly or directly on the first chamber 3 by the drive unit 5 can be exerted from any direction. The only decisive criterion here is that the volume of the first chamber 3 can be increased and decreased by the drive unit 6.

Figure 8:
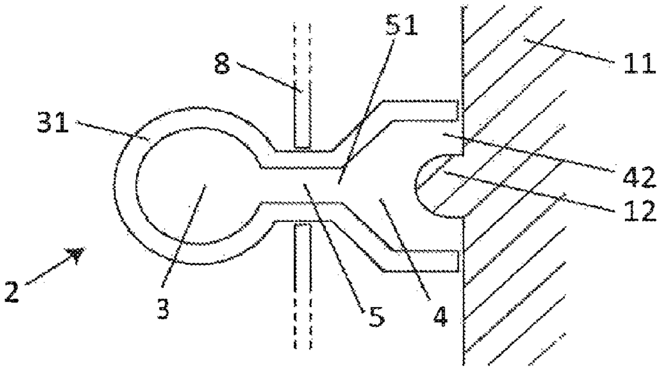
FIG. 8 shows a cross section through a pressure field generating arrangement of a third aspect of the present invention.

FIG. 8 shows a third aspect of a one-piece structure of the pressure field generating arrangement 2. Here, a resilient material such as silicone or rubber can be used as material for the chambers 3 and 4. The advantage here is that any gaps that are dubious from the point of view of hygiene are avoided, and the cost of manufacture is reduced. The pressure field generating arrangement 2 can be joined to the housing 8 by adhesion or screws in this case too. A change in the volume of the first chamber 3 occurs here in a manner analogous to that described in conjunction with FIG. 7.

Figure 9:
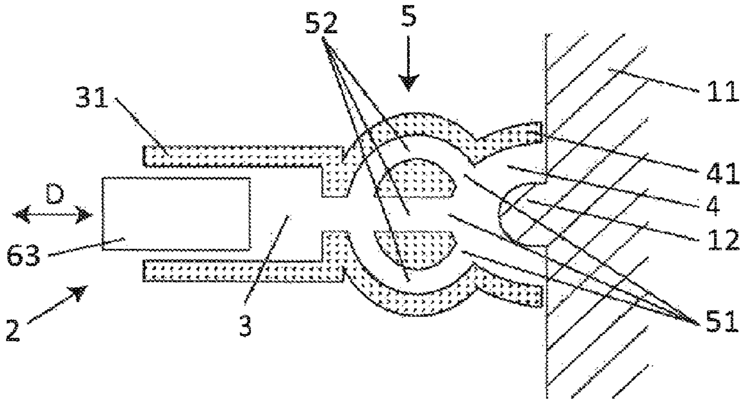
FIG. 9 shows a cross section through a pressure field generating arrangement of a fourth aspect of the present invention.

FIG. 9 shows a fourth aspect of an alternative construction of the pressure field generating arrangement 2. Here, the second chamber 4, a plurality of connection elements 5, and partial sections of the wall 31 of the first chamber 3 are constructed in one piece. Alternatively, the pressure field generating arrangement 2 can also be constructed in two or more pieces from individual components, while retaining the geometric shape of FIG. 9, in a similar way to that shown in FIG. 4 or 7.

In this case, the volume in the chamber 3 is changed in a manner similar to a piston pump, although there are no valves of any kind here. Thus, a piston 63 is moved back and forth by the drive unit, for example an electric motor or electromagnet, in the directions of the double arrow D. This type of drive has the advantage that the volume of the first chamber 3 can be reduced to zero or approximately zero in a simple manner, thus allowing the first chamber 3 to be almost completely emptied.

The embodiment of the connection element 5, with a plurality of channels 52 and openings 51, results in a distribution of the pressure field over a plurality of concentration points. While the embodiment of the connection element 5 with only one channel, as described in conjunction with FIG. 6, results in the formation of a highly concentrated medium or air flow onto a target area, the embodiment of the connection element 5 shown in FIG. 9 allows the medium or air flow to be distributed over a plurality of target areas. In this way, the flow can for example be blown against the clitoris 11 not just on its glans, but evenly from a plurality of sides. Depending on the application, this distribution of the air flow concentration to a plurality of areas can help to avoid overstimulation and/or help to increase the stimulation area.

Figure 10A:
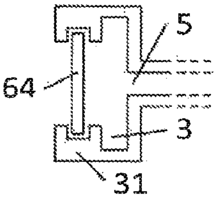
FIGS. 10 *a*), *b*) and *c*) show cross sections through a pressure field generating arrangement of a fifth aspect of the present invention.
Figure 10B:
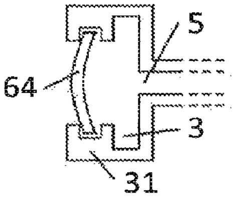
Figure 10C:
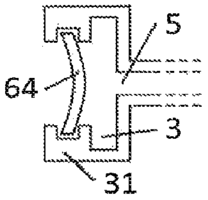

FIGS. 10*a* to 10*c* show (partial) cross sections of one embodiment of a construction of the pressure field generating arrangement 2 with a bending element 64 as the drive for changing the volume in the first chamber 3. The bending element 64 can for example be a conventional piezoelectric bending element, which is deformed or bent once a voltage is applied. In this embodiment, the wall 31 of the first chamber 3 takes a rigid or stiff form, while the bending element 64 is made to fit suitably against the sides of the first chamber 3. The transition points between the bending element 64 and the wall 31 are in this case sealed (resiliently joined by adhesion, for example). In this construction, the drive for the pressure field generating arrangement 2 is already integrated therein, and an external drive is not required. An electric motor with a cam is not needed, for example. This allows, inter alia, the reduction of any disruptive natural resonances due to movement of the cam of the stimulation device.

FIG. 10*a* shows in detail the pressure field generating arrangement 2 with the bending element 64 in a neutral position. Thus, the volume of the first chamber 3 with the bending element 64 in the neutral position is the standard volume. FIG. 10*b* furthermore shows the first chamber 3 with an excited and, consequently, outwardly bent bending element, for which reason the volume of the first chamber 3 has increased; consequently, a negative pressure prevails in the pressure field generating arrangement 2. FIG. 10*c* shows a bending element of the first chamber 3 excited in the opposite direction to FIG. 10*b*, for which reason the volume of the first chamber 3 has decreased; consequently, a positive pressure prevails in the pressure field generating arrangement 2.

Figure 11:
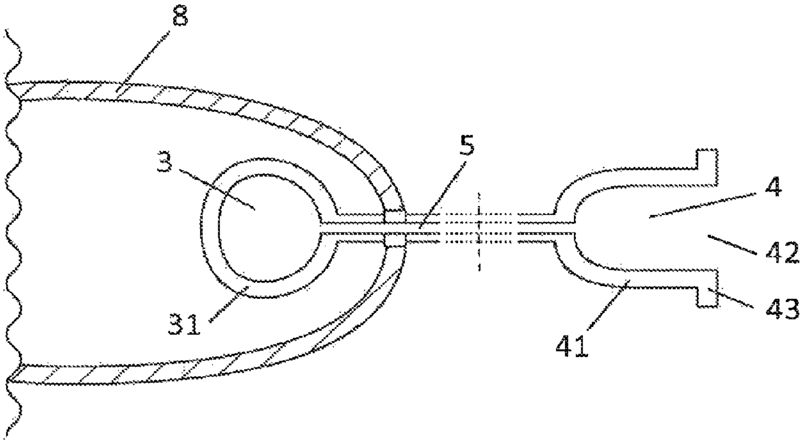
FIG. 11 shows a partial cross section through a second embodiment of the stimulation device according to the invention.
Figure 12A:
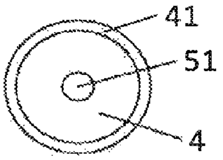
FIGS. 12 *a*) to *f*) show various bottom and side views of further aspects of a second chamber of the present invention.
Figure 12B:
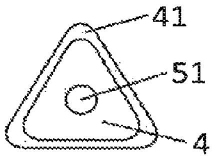
Figure 12C:
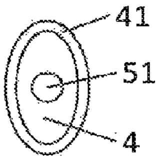
Figure 12D:
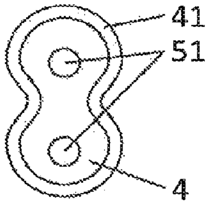
Figure 12E:
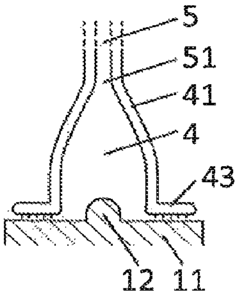
Figure 12F:
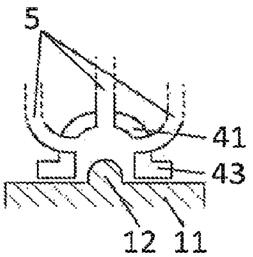

FIG. 11 shows a second embodiment of a spatially separated arrangement of the chambers 3 and 4 of the pressure field generating arrangement 2. The chambers 3 and 4 are in this case connected via an extended connection element 5, which can be a relatively long flexible hose or a pipe, which may also be rigid. For example, the connection element 5 may be 0.5 m in length. This enables the housing 8 to be held in one hand while the other hand holds the second chamber 4 on the body part 11 to be stimulated; or the housing 8 may simply be laid aside, while the user holds only the second chamber 4 in both hands. Alternatively, the appendage 140 can be inserted into a body part, in which case it is no longer necessary for the stimulation device 1 to be held in the hand.

FIGS. 12 *a*) to 12 *f*) show various bottom and side views of further aspects of the second chamber 4 in accordance with one or more embodiments. In detail, FIG. 12 *a*) shows a bottom view of a circular second chamber 4 with a central opening 51; FIG. 12 *b*) shows a bottom view of a triangular second chamber 4 with a central opening 51; FIG. 12 *c*) shows a bottom view of an oval second chamber 4 with a central opening 51; and FIG. 12 *d*) shows a bottom view of an approximately eight-shaped second chamber 4 with two openings 51 arranged offset from the center. FIG. 12 *e*) furthermore shows a side cross section of a second chamber 4, wherein the second chamber 4 additionally has an extended contact surface 43 for the skin or a support part 43 to improve the sealing function of the second chamber 4 on the skin. The extended contact surface 43 may moreover have grooves or projections that improve the sealing function even further. FIG. 12 *f*) shows a side cross section of a second chamber 4 having a plurality of separate connection elements 5 and an extended contact surface resulting from the support part 43.

The shape of the second chamber 4 can thus be fundamentally adjusted to the anatomy of the erogenous zone to be stimulated. The shape of the chamber 4 in FIG. 12 *a*) is, for example, adjusted to the round shape of the breast, while the shape of chamber 4 in FIG. 12 *c*) is better suited to the shape of the female vulva. Furthermore, the shape of the second chamber 4 also determines how pronounced the pressure field is. The size of the second chamber 4 in relation to the volume displaced from the first chamber 3 thus determines the level of the achievable negative or positive pressure. Furthermore, the proximity of the opening 51 of the connection element 5 to the area of skin to be stimulated can also be used to determine the intensity of the massaging effect on said area of skin. A plurality of openings 51, cf. FIG. 12 *d*), allows the massaging effect to be distributed over a plurality of areas. Thus, for example, the clitoris can be stimulated less directly at the very sensitive clitoral glans (cf. FIG. 12 *e*)) but more at the areas surrounding the clitoral glans, in order to prevent overstimulation of the clitoris.

Figure 13:
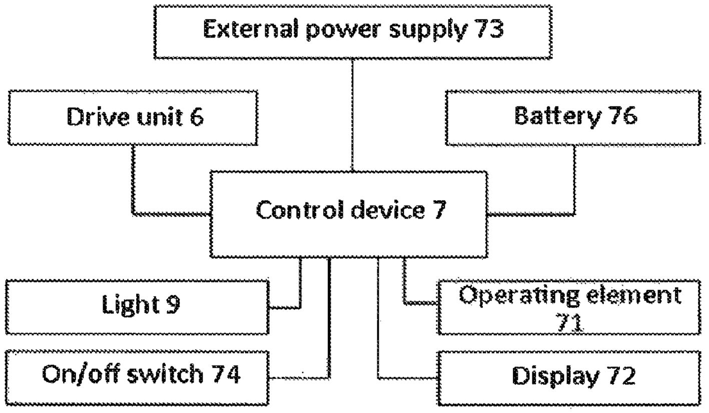
FIG. 13 shows a block diagram of an embodiment of the present invention.

FIG. 13 shows a block diagram of an example of the functional construction of an embodiment having a control device 7, a drive unit 6, a light 9, an on/off switch 74, operating elements 71, a battery 76 and an external power supply 73.

The control device 7, which for example has a microcontroller or is hardwired, initially controls the power supply to all the consumers of the stimulation device 1 and optionally controls a process of charging and discharging the battery 76 and/or battery management. In particular, the control device 7 controls the excitation of the drive unit 6, such as the size of the deflection, the frequency, the modulation, etc.

Optionally provided operating elements 71 serve to set the mode of the device, i.e. to set the modulation pattern of the pressure field. The operating elements 71 may for example take the form of at least one push button, at least one rotary switch, or at least one touch-sensitive switch. Furthermore, the operating elements 71 may emit optical feedback for the purpose of confirmation, for example by means of light emitting diodes (LEDs) integrated in the switch.

An optional display 72 serves to inform the user of the device state and/or the set condition. The display 72 may for example take the form of a plurality of light emitting diodes or an LCD display. The displayed information may for example be the charging condition of an optional battery, or the current setting of the modulation pattern.

Furthermore, the control device 7 may have a memory in which at least one modulation or stimulation pattern (described in more detail in conjunction with FIGS. 14 *a*) to *d*)) is stored. Excitation of the drive unit 6 can now be activated via the operating elements 71 in accordance with this previously stored stimulation pattern, depending on the choice made by the user of the stimulation device 1. The stimulation pattern of the pressure field can also be optionally and individually generated and stored by the user via the operating elements.

A socket (not shown in detail) can serve to supply external power to the stimulation device 1 via an external plug that is for example connected to an external mains adapter. In order to ensure that the stimulation device 1 is splash-proof, it is also possible, instead of the socket, to provide an electromagnetically inductive transformer that allows power to be supplied to the stimulation device 1 without an electrically conductive contact. Preferably, the stimulation device 1 moreover has a battery, for example a nickel metal hydride battery (NiMH), for wireless operation. Alternatively, a (relatively long) power supply cable may lead out of the stimulation device.

Figure 14A:
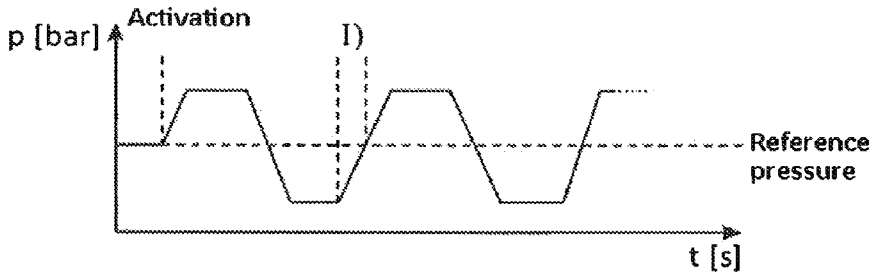
FIGS. 14 *a*) to *c*) show graphs of various pressure modulation patterns of the present invention.
Figure 14B:
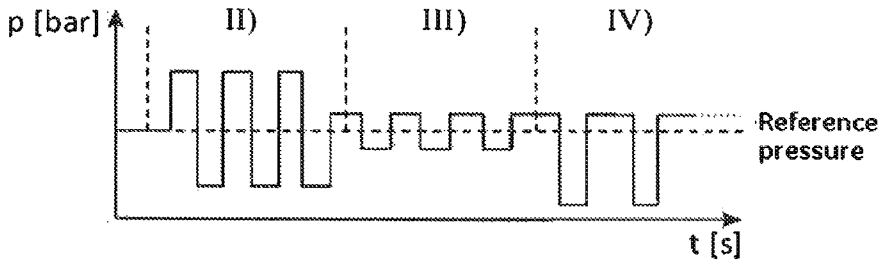
Figure 14C:
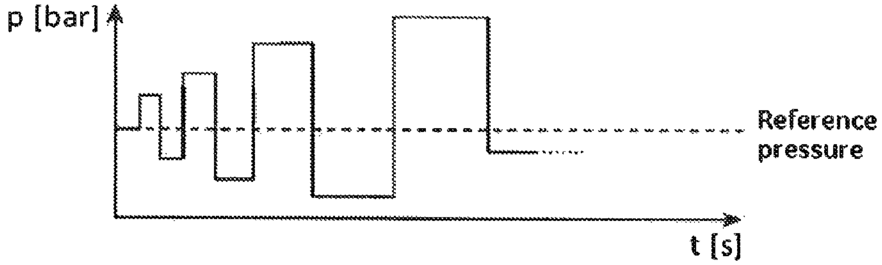

FIG. 14 *a*) shows the sequence over time of overall pressure p in the pressure field generating arrangement (2) when the latter is used for stimulation. The broken line indicates the reference pressure, for example the currently prevailing atmospheric pressure, outside the pressure field generating arrangement (2). If the second chamber 4 is now placed on the body part 11 to be stimulated, the initially prevailing ambient pressure remains approximately constant in the pressure field generating arrangement (2). It is assumed that the second chamber 4 is placed on the body part to be stimulated such that it is largely air-tight. Once the stimulation device is activated, the drive unit 6 is activated or excited by the control device 7 in accordance with a previously stored stimulation pattern. Accordingly, the volume of the first chamber 3 and thus the overall pressure in the pressure field generating arrangement 2 are changed, with the changes in pressure being modulated onto the reference pressure. The pressure or stimulation pattern shown as an example in FIG. 14 *a*) develops a pulsed, regular pressure field. In phases of pressure increase, air is blown against or massages the erogenous zone to be stimulated, whereas at times when a negative pressure prevails the blood circulation in the body part 11, for example the clitoris, is favored. Thus, there are time periods (designated in FIG. 14 *a*) as I)) in which a negative pressure prevails while the clitoris is simultaneously being indirectly massaged.

FIG. 14 *b*) shows three examples of alternative stimulation patterns. Thus, the area designated as II) shows a pulsed stimulation pattern of high amplitude. The area designated as III) shows a pulsed stimulation pattern of low amplitude. Furthermore, the area designated as IV) illustrates a stimulation pattern which is irregular as regards sequence over time and asymmetrical in amplitude. The patterns can be varied, depending on the effect on the body/application and in accordance with the wishes of the individual.

FIG. 14 *c*) shows a further example of an alternative stimulation pattern. Here, the intensity of the pressure may increase with time in order to adjust to the user's state of excitement.

In addition to the embodiments that have been explained, further constructional principles are allowed. For example, different arrangements or constructions of the first chamber 3 may be combined as desired with different embodiments of the second chamber 5 or the connection element 5. For example, the first chamber 3 having the drive in FIG. 10 can be combined with the second chamber in FIG. 12 *f*).

Although only one first chamber 3 is shown in all embodiments, two or more first chambers 3 may also be provided, which are then driven accordingly simultaneously or with a time delay such that their volume is changed in order to build up a pressure field.

Although only one opening from the first chamber 3 to the connection element 5 is shown in all embodiments, a plurality of openings for a connection element 5 or indeed a plurality of openings for a plurality of connection elements 5 may also be provided in the first chamber 3.

A stimulation device 1 can have a plurality of pressure field generating arrangements 2. Thus, for example, two pressure field generating arrangements may be provided in order to stimulate two erogenous zones simultaneously.

The stimulation patterns can differ from the patterns shows in FIGS. 14 *a*), *b*) and *c*), provided they have a sequence of positive and negative pressures over time. For example, a relatively long-lasting negative pressure can initially be built up at the beginning or after activation of the device (for example 3 minutes), in order to effectively increase the blood circulation in the zone to be stimulated, after which pulses of negative and positive pressures of slowly increasing amplitude follow.

LIST OF REFERENCE NUMERALS

1 Stimulation device
2 Pressure field generating arrangement
3 First chamber
4 Second chamber
5 Connection element
6 Drive unit
7 Control device
8 Housing
9 Light
11 Body part
12 Clitoris
31 Wall of the first chamber
32 Holder
41 Wall of the second chamber
42 Opening of the first chamber
43 Contact surface
51 Opening from the connection element to the second chamber
61 Drive shaft
62 Cam
63 Piston
64 Bending element
71 Operating element
72 Display
73 Power supply
74 On/off switch
76 Battery
77 Control board
140 Appendage
141 Joint
142 Vibration device

The invention claimed is:

1. A stimulation device, comprising:
- a chamber having a flexible wall portion;
- a drive unit in physical communication with the flexible wall portion so as to cause deflections of the flexible wall portion in opposing directions, thereby resulting in a changing volume of the chamber,
- the changing volume of the chamber resulting in modulated positive and negative pressures with respect to a reference pressure;
- an opening for applying the modulated positive and negative pressures to a body part;
- a control device for controlling the drive unit; and
- an appendage, wherein the appendage is a dildo configured to be inserted into a vagina.

2. The stimulation device as recited in claim 1, wherein the appendage is a handle for holding the stimulation device.

3. The stimulation device as recited in claim 1, wherein the opening is further for placing over the body part.

4. The stimulation device as recited in claim 1, wherein the body part is a clitoris.

5. The stimulation device as recited in claim 1, further comprising a second chamber.

6. The stimulation device as recited in claim 1, wherein the flexible wall portion is integral with the chamber.

7. The stimulation device as recited in claim 1, wherein the flexible wall portion comprises silicone.

8. The stimulation device as recited in claim 1, wherein the stimulation device has no valves.

9. The stimulation device as recited in claim 1, wherein the stimulation device is a portable hand-held device.

10. The stimulation device as recited in claim 1, wherein the stimulation device is battery powered.

11. The stimulation device as recited in claim 1, further comprising:
- a water resistant housing comprising acrylonitrile butadiene styrene (ABS).

12. A method comprising:
- causing deflections of a flexible wall portion of a chamber of a stimulation device in opposing directions, thereby resulting in a changing volume of the chamber,
- the changing volume of the chamber resulting in modulated positive and negative pressures with respect to a reference pressure; and
- applying the modulated positive and negative pressures to a body part through an opening, wherein the stimulation device is positioned by a user for applying the modulated positive and negative pressures using an appendage of the stimulation device, wherein the appendage is a dildo configured to be inserted into a vagina.

13. The method as recited in claim 12, wherein the appendage is a handle for holding the stimulation device.

14. The method as recited in claim 12, wherein the changing volume of the chamber results in the modulated positive and negative pressures in a second chamber.

15. The method as recited in claim 12, wherein the body part is a clitoris and the opening is placed over the clitoris.

16. The method as recited in claim 12, wherein the flexible wall portion is integral with the chamber.

17. A stimulation device, comprising:
- a pressure field generator having a flexible wall portion;
- a drive unit in physical communication with the flexible wall portion so as to cause deflections of the flexible wall portion in opposing directions, thereby resulting in a changing volume of the pressure field generator,
- the changing volume of the pressure field generator resulting in modulated positive and negative pressures with respect to a reference pressure;
- an opening for applying the modulated positive and negative pressures to a body part;
- a control device for controlling the drive unit; and
- an appendage, wherein the appendage is a dildo configured to be inserted into a vagina.

18. The stimulation device as recited in claim 17, wherein the appendage is a handle for holding the stimulation device.

19. The stimulation device as recited in claim 17, wherein the body part is a clitoris and the opening is further for placing over the body part.

20. The stimulation device as recited in claim 17, wherein the body part is a clitoris.

21. The stimulation device as recited in claim 17, wherein the pressure field generator comprises a first chamber and a second chamber.

22. The stimulation device as recited in claim 17, wherein the flexible wall portion is integral with the pressure field generator.

23. The stimulation device as recited in claim 17, wherein the stimulation device has no valves.

24. The stimulation device as recited in claim 17, wherein the stimulation device is a portable hand-held device.

25. The stimulation device as recited in claim 17, wherein the stimulation device is battery powered.

26. A method comprising:
- causing deflections of a flexible wall portion of a pressure field generator of a stimulation device in opposing directions, thereby resulting in a changing volume of the pressure field generator,
- the changing volume of the pressure field generator resulting in modulated positive and negative pressures with respect to a reference pressure; and
- applying the modulated positive and negative pressures to a body part through an opening, wherein the stimulation device is positioned by a user for applying the modulated positive and negative pressures using an appendage of the stimulation device, wherein the appendage is a dildo configured to be inserted into a vagina.

27. The method as recited in claim 26, wherein the appendage is a handle for holding the stimulation device.

28. The method as recited in claim 26, wherein causing deflections in a flexible wall portion of a pressure field generator in opposing directions comprises:
- causing deflections in the flexible wall portion of a first chamber of the pressure field generator, thereby resulting in the modulated positive and negative pressures in a second chamber of the pressure field generator.

29. The method as recited in claim 26, wherein the body part is a clitoris and the opening is placed over the clitoris.

30. The method as recited in claim 26, wherein the flexible wall portion is integral with the pressure field generator.

* * * * *